(12) United States Patent
Tanaka et al.

(10) Patent No.: US 12,324,660 B2
(45) Date of Patent: Jun. 10, 2025

(54) THREE-DIMENSIONAL SCANNER, CONTROL METHOD, AND RECORDING MEDIUM FOR RECORDING PROGRAMS

(71) Applicant: J. MORITA MFG. CORP., Kyoto (JP)

(72) Inventors: Tsuyoshi Tanaka, Kyoto (JP); Keisuke Sorimoto, Kyoto (JP)

(73) Assignee: J. MORITA MFG. CORP., Kyoto (JP)

( * ) Notice: Subject to any disclaimer, the term of this patent is extended or adjusted under 35 U.S.C. 154(b) by 179 days.

(21) Appl. No.: 18/061,038

(22) Filed: Dec. 2, 2022

(65) Prior Publication Data
US 2023/0200681 A1 Jun. 29, 2023

(30) Foreign Application Priority Data
Dec. 10, 2021 (JP) ................................ 2021-200783

(51) Int. Cl.
*A61B 5/107* (2006.01)
*A61B 5/00* (2006.01)
(Continued)

(52) U.S. Cl.
CPC .......... *A61B 5/1079* (2013.01); *A61B 5/0088* (2013.01); *A61B 5/1077* (2013.01);
(Continued)

(58) Field of Classification Search
CPC ... A61B 5/1079; A61B 5/0088; A61B 5/1077; A61C 9/0066; G01B 11/24; G01B 11/25;
(Continued)

(56) References Cited

U.S. PATENT DOCUMENTS 9,814,548 B2 * 11/2017 Eom .................... A61C 9/0066
10,772,506 B2 * 9/2020 Atiya ..................... G01B 11/24
(Continued)

FOREIGN PATENT DOCUMENTS

CN 211485040 U * 9/2020 ............. A61C 19/04
JP 2008-46361 A 2/2008
(Continued)

OTHER PUBLICATIONS

Kim, Kyu-Ha, and Sang-Hyun Lee. "Development of 3D scanner using structured light module based on variable focus lens." International Journal of Advanced Culture Technology 8.3 (2020): 260-268. (Year: 2020).*
(Continued)

*Primary Examiner* — Mohamed K Amara
*Assistant Examiner* — Noah J. Haney
(74) *Attorney, Agent, or Firm* — Oblon, McClelland, Maier & Neustadt, L.L.P.

(57) ABSTRACT

The present disclosure provides a three-dimensional scanner for acquiring three-dimensional shape information of an object using focusing, including a light source configured to emit light from an emission end face of a housing to the object; a sensor configured to detect light from the light source reflected by the object; a variable focus lens that is provided between the object and the sensor and that changes a focal position based on the object; and a controller configured to change the focal position of the variable focus lens in a process of acquiring the three-dimensional shape information of the object, wherein the controller is configured to change an amount of light from the light source reflected by the object and reaching the sensor based on the focal position of the variable focus lens.

20 Claims, 12 Drawing Sheets

(51) Int. Cl.
  *A61C 9/00* (2006.01)
  *G01B 11/24* (2006.01)
  *G01B 11/25* (2006.01)
  *G01B 21/04* (2006.01)
  *G02B 3/14* (2006.01)
  *G02B 7/28* (2021.01)

(52) U.S. Cl.
  CPC ............ *A61C 9/0066* (2013.01); *G01B 11/24* (2013.01); *G01B 11/25* (2013.01); *G01B 11/2504* (2013.01); *G01B 11/2518* (2013.01); *G02B 3/14* (2013.01); *G01B 21/042* (2013.01); *G02B 7/28* (2013.01); *G02B 2207/117* (2013.01)

(58) Field of Classification Search
  CPC ............ G01B 11/2504; G01B 11/2518; G01B 21/042; G02B 3/14; G02B 7/28; G02B 2207/117
  USPC .......................................................... 356/601
  See application file for complete search history.

(56) References Cited

U.S. PATENT DOCUMENTS

| | | | |
|---|---|---|---|
| 11,060,852 B2 | 7/2021 | Sorimoto | |
| 11,563,929 B2 * | 1/2023 | Saphier | A61C 9/006 |
| 2001/0043335 A1 * | 11/2001 | Norita | G01B 11/2518 356/601 |
| 2007/0103893 A1 | 5/2007 | Tanaka | |
| 2011/0080576 A1 * | 4/2011 | Thiel | G01J 3/021 356/73 |
| 2012/0199655 A1 | 8/2012 | Fukuba | |
| 2014/0118687 A1 | 5/2014 | Ohban et al. | |
| 2016/0045291 A1 * | 2/2016 | Verker | G02B 21/006 356/364 |
| 2016/0267677 A1 | 9/2016 | Komatsu | |
| 2018/0125338 A1 * | 5/2018 | Pfeiffer | G01B 11/2513 |
| 2018/0267291 A1 * | 9/2018 | Mikami | A61B 1/00188 |
| 2019/0293414 A1 * | 9/2019 | Sorimoto | G01B 11/2518 |
| 2021/0325649 A1 * | 10/2021 | Segev | A61B 3/0008 |
| 2022/0369907 A1 * | 11/2022 | Deichmann | A61B 5/0088 |

FOREIGN PATENT DOCUMENTS

| | | | | |
|---|---|---|---|---|
| JP | 2010-54870 A | 3/2010 | | |
| JP | 4473337 B1 | 6/2010 | | |
| JP | 2010-243438 A | 10/2010 | | |
| JP | 2014-83397 A | 5/2014 | | |
| JP | 5654583 B2 | 1/2015 | | |
| JP | 2016-167698 A | 9/2016 | | |
| JP | 2018-4282 A | 1/2018 | | |
| JP | 2018-151239 A | 9/2018 | | |
| KR | 20140077380 A * | 6/2014 | | A61C 19/04 |
| WO | WO 2005/103658 A1 | 11/2005 | | |
| WO | WO 2010/145669 A1 | 12/2010 | | |
| WO | WO-2018164538 A1 * | 9/2018 | | A61B 5/00 |

OTHER PUBLICATIONS

Extended European Search Report issued May 26, 2023 in European Patent Application No. 22211958.8, 6 pages.
Extended European Search Report issued Jul. 12, 2023 in European Patent Application No. 22211958.8, 5 pages.
S. Logozzo, et al., "A Comparative Analysis of Intraoral 3d Digital Scanners for Restorative Dentistry," The Internet Journal of Medical Technology, vol. 5, No. 1, XP055438343, 2008, 18 pages.
Japanese Office Action issued Dec. 26, 2023 in Japanese Patent Application No. 2021-200783 (with unedited computer-generated English Translation), 9 pages.

* cited by examiner

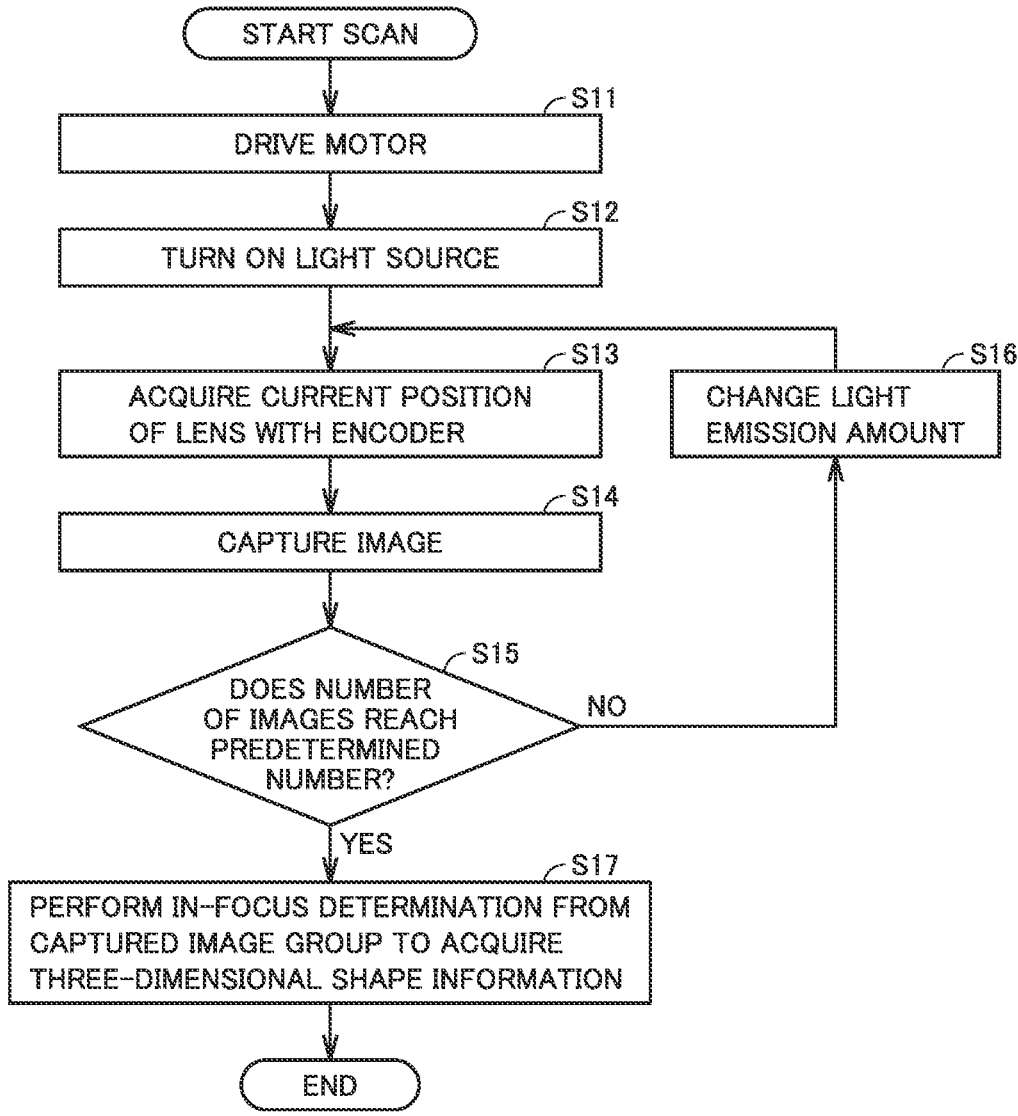

THREE-DIMENSIONAL SCANNER, CONTROL METHOD, AND RECORDING MEDIUM FOR RECORDING PROGRAMS

BACKGROUND OF THE DISCLOSURE

Field of the Disclosure

The present disclosure relates to a three-dimensional scanner for acquiring three-dimensional shape information of an object, a control method, and a recording medium for recording programs.

Description of the Background Art

In the field of dentistry, in order to digitally design a dental prosthesis or the like on a computer, it has been recently required to acquire three-dimensional shape information of a tooth, and a three-dimensional scanners (intraoral scanners) have been put into practical use (Japanese Patent No. 5654583). A three-dimensional scanner disclosed in Japanese Patent No. 5654583 is a handheld scanner that acquires three-dimensional shape information of an object by using the principle of a "dot product" which is a type of focusing method. Specifically, in the three-dimensional scanner, light having a pattern such as a linear pattern or a checkered pattern (hereinafter also referred to as a pattern) is projected onto the surface of an object, and a best focusing distance is determined from a plurality of images obtained by imaging the object at a plurality of times while changing the focusing position, thereby acquiring three-dimensional shape information of the object.

SUMMARY

However, for some types of objects to be imaged by a three-dimensional scanner, it has been impossible to acquire images in which patterns projected onto the objects are clearly reflected, so that it has been difficult to accurately determine the focal position based on the focusing method. As a result, there has been a possibility that the measurement accuracy of three-dimensional shape information obtained by imaging objects may deteriorate in the three-dimensional scanners.

The present disclosure has been made to solve the above problem and to provide a three-dimensional scanner capable of improving the measurement accuracy of three-dimensional shape information, a control method, and a recording medium for recording programs.

A three-dimensional scanner according to the present disclosure is a three-dimensional scanner for acquiring three-dimensional shape information by using a focusing method. The three-dimensional scanner comprises a light source that emits light from an emission end face of a housing to an object, a sensor that detects light from the light source which is reflected by the object, a variable focus lens that is provided between the object and the sensor and changes a focal position for the object, and a controller that performs control to change the focal position of the variable focus lens in a process of acquiring the three-dimensional shape information of the object. The controller changes an amount of light from the light source reflected by the object and reaching the sensor based on the focal position of the variable focus lens.

A control method according to the present disclosure is a control method for a three-dimensional scanner that comprises a light source that emits light from an emission end face of a housing to an object, a sensor that detects light from the light source reflected by the object, a variable focus lens that is provided between the object and the sensor and changes a focal position for the object, and a controller that performs control to change the focal position of the variable focus lens in a process of acquiring the three-dimensional shape information of the object and acquires three-dimensional shape information of the object by a focusing method. The control method comprises: acquiring information on the focal position of the variable focus lens and changing an amount of light from the light source reflected by the object and reaching the sensor based on the acquired information.

Programs to be recorded in a recording medium according to the present disclosure are programs to be executable by a computer included in a three-dimensional scanner comprising a light source that emits light from an emission end face of a housing to an object, a sensor that detects light from the light source reflected by the object, and a variable focus lens that is provided between the object and the sensor to change a focal position for the object, the three-dimensional scanner acquiring three-dimensional shape information by using a focusing method. The program causes the computer to change a focal position of the variable focus lens in a process of acquiring the three-dimensional shape information of the object and change an amount of light from the light source reflected by the object and reaching the sensor based on the focal position of the variable focus lens.

The foregoing and other objects, features, aspects and advantages of the present disclosure will become more apparent from the following detailed description of the present disclosure when taken in conjunction with the accompanying drawings.

BRIEF DESCRIPTION OF THE DRAWINGS

FIG. 8 is a flowchart for illustrating dimming control of the light source of the three-dimensional scanner according to the first embodiment.

DETAILED DESCRIPTION

Embodiments according to the present disclosure will be described hereinafter with reference to drawings.

First Embodiment

A three-dimensional scanner according to a first embodiment is a three-dimensional scanner (intraoral scanner) for acquiring three-dimensional shape information of intraoral tissue (for example, a tooth). Note that even in the case of an intraoral scanner, it may acquire three-dimensional shape information on not only a tooth in an oral cavity, but also a gum, a mucous membrane, a prepared dental prosthesis, a scan body for implant, an orthodontic appliance, and various dental technical materials. Further, the three-dimensional scanner is not limited to the intraoral scanner and can be applied to other three-dimensional scanners having similar configurations. For example, the present disclosure can be applied to a three-dimensional scanner which is capable of imaging the inside of a human ear as well as the inside of the oral cavity and acquiring three-dimensional shape information of the inside of an external ear.

[Configuration of Three-dimensional Scanner]

Figure 1:
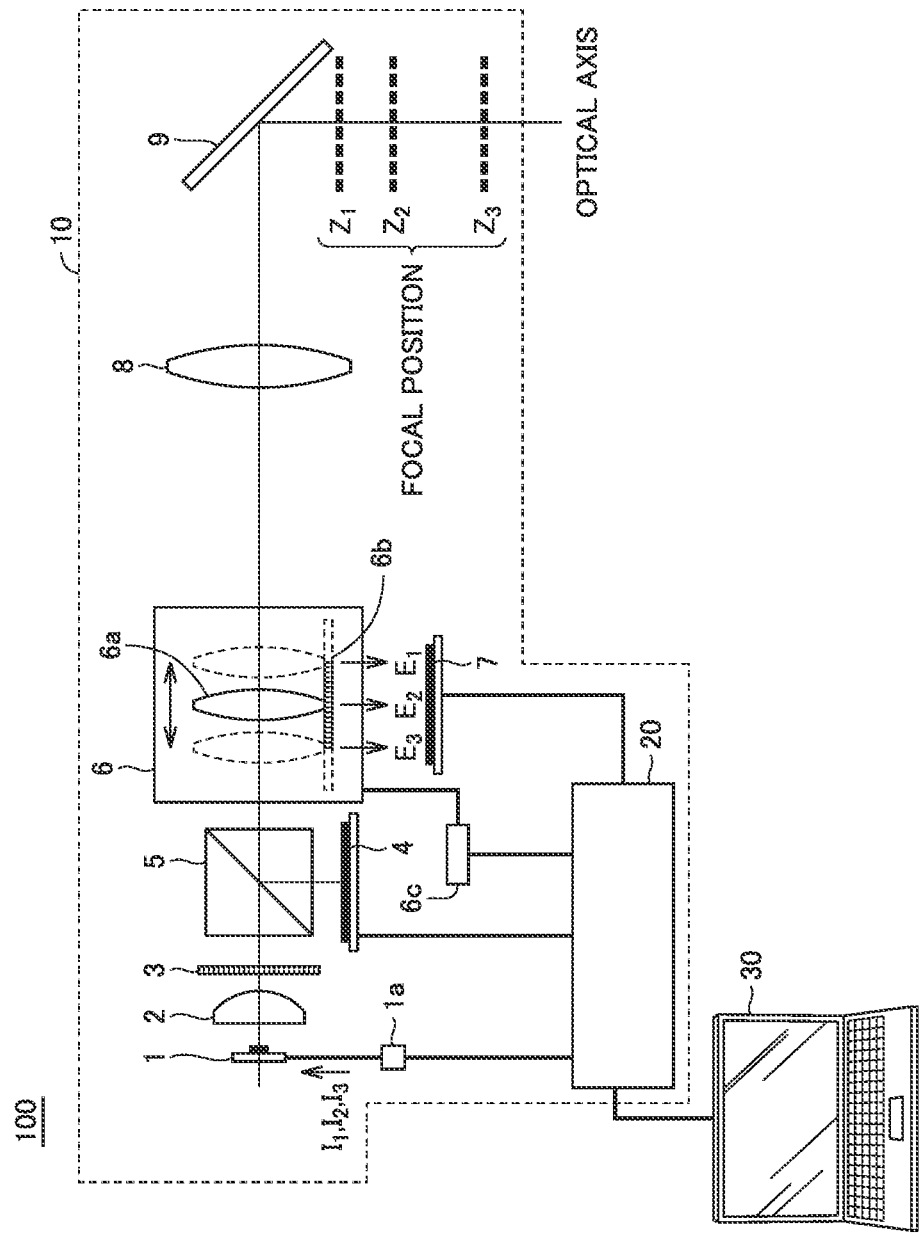
FIG. 1 is a schematic diagram showing a configuration of a three-dimensional scanner according to a first embodiment.

FIG. 1 shows a configuration of a three-dimensional scanner 100. Three-dimensional scanner 100 shown in FIG. 1 includes a handpiece 10 for imaging the inside of an oral cavity, and a computer 30 which is connected to handpiece 10 and processes and displays acquired data. The three-dimensional scanner may be configured so as to perform all processing within handpiece 10 and output only display data to an external monitor.

Figure 2:
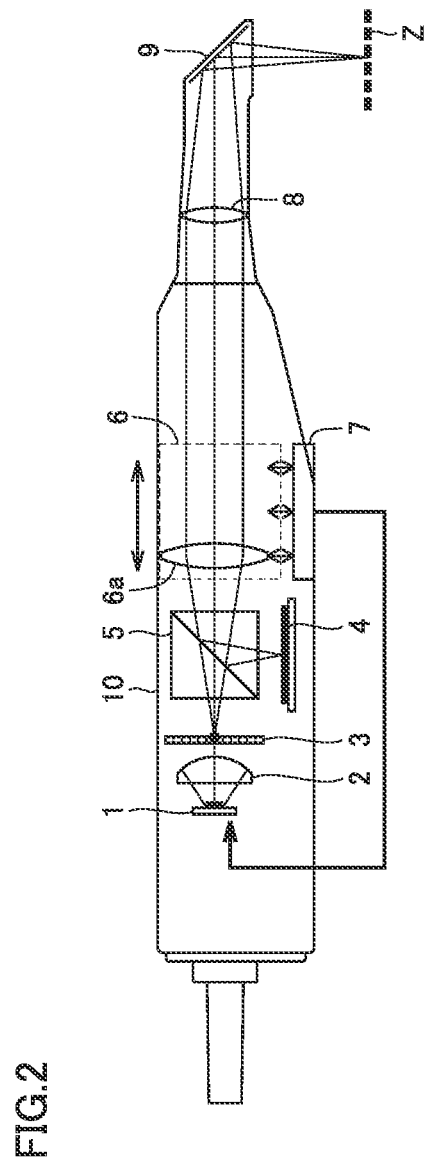
FIG. 2 is a schematic diagram for illustrating an optical configuration in a handpiece according to the first embodiment.

Handpiece 10 includes an optical configuration for projecting a pattern onto a tooth as an object and detecting reflected light from the pattern-projected object, and a controller 20 for processing a captured image to acquire three-dimensional shape information. FIG. 2 shows the optical configuration inside handpiece 10. The optical configuration inside handpiece 10 includes a light source 1, a first lens 2, a pattern generator 3, an optical sensor 4, a beam splitter 5, a variable focus lens 6, a focal position detector 7, a second lens 8, and a mirror 9. In addition to these components, handpiece 10 may be provided with optical components such as another lens, a diaphragm, an optical filter, a window, a polarizing element, etc. as required.

Light source 1 is, for example, an LED (Light Emitting Diode). As described later, light source 1 can change a light emission amount. For example, in the case of an LED, the light emission amount can be adjusted by changing the amount of current to be supplied from a driver circuit $1a$ to the LED. Note that light source 1 is not limited to a point light source in which single LED, laser element or the like is provided, and may be an array light source in which a plurality of element light sources such as LEDs or laser elements are arranged on a substrate. In one embodiment, a multicolor light source such as three primary color LEDs may be used. Note that it is also possible to adjust the light emission amount of light source 1 by temporally modulating the LED under PWM (Pulse Width Modulation) control and changing the duty cycle of the modulated wave, or by changing the number of elemental light sources to be turned on in an array light source configured by a plurality of elemental light sources. Unless otherwise specified in the present disclosure, when "change of the amount of current" is expressed, it is assumed to include the above-described PWM modulation and the change in the number of element light sources to be turned on in the array light source.

First lens 2 uniformizes light from light source 1 and irradiates pattern generator 3 with the light. Pattern generator 3 is a filter having, for example, a pattern such as a linear pattern or a checkered pattern, and generates a pattern to be projected onto the surface of the object.

Optical sensor 4 is, for example, a CCD (Charge Coupled Device) image sensor, a CMOS (Complementary Metal-Oxide-Semiconductor) image sensor or the like. Optical sensor 4 detects light that passes through pattern generator 3, is projected onto the object, and is reflected by the object. Beam splitter 5 is an optical component for separating an optical path extending from light source 1 to the object and an optical path extending from the object to optical sensor 4 from each other.

In variable focus lens 6, a focus lens $6a$ is fixed to a slider, and the slider moves on a rail $6b$ extending in an optical axis direction to change a focal position of the object and a focal position of optical sensor 4. Note that the focal point generally includes two focal points of an "object-side focal point" which is a focal point on the object, and an "image-side focal point" which is a focal point on optical sensor 4, and unless otherwise specified, the focal position described in the present disclosure is the position of the "object-side focal point". Specifically, in variable focus lens 6, focus lens $6a$ fixed to the slider reciprocates among positions $E_1$ to $E_3$ by driving a motor with a drive signal supplied from a motor driver $6c$. By changing the position of focus lens $6a$ from the positions $E_1$ to $E_3$, variable focus lens 6 changes the focal position between a focal position $Z_1$ close to the emission end face of handpiece 10 (housing) and a focal position $Z_3$ far from the emission end face.

Focal position detector 7 detects the focal position of variable focus lens 6. Focal position detector 7 does not directly detect the focal positions $Z_1$ to $Z_3$, but indirectly detects the focal positions $Z_1$ to $Z_3$ by detecting the positions $E_1$ to $E_3$ of the focus lens $6a$ corresponding to the focal positions $Z_1$ to $Z_3$. Specifically, focal position detector 7 is an optical encoder (lens position sensor) for detecting the positions $E_1$ to $E_3$ of the focus lens $6a$. Note that focal position detector 7 may be a detector other than the optical encoder as long as it can detect the positions $E_1$ to $E_3$ of focus lens 6a. For example, position detection using a magnetic sensor or the like can be applied.

In three-dimensional scanner 100, as described later, the light emission amount of light source 1 is changed based on the focal position detected by focal position detector 7. Specifically, in three-dimensional scanner 100, the light emission amount of light source 1 is changed by changing current amounts $I_1$ to $I_3$ to be supplied to light source 1 based on the positions $E_1$ to $E_3$ of focus lens 6a detected by the optical encoder.

Light that has passed through variable focus lens 6 passes through second lens 8 and mirror 9, and then is applied to the object. Second lens 8 is an optical component for focusing, onto the object, the light that has passed through variable focus lens 6. Mirror 9 is an optical component for changing the directions of light from light source 1 and light reflected by the object. The configurations of second lens 8 and mirror 9 are examples, and the configurations thereof may be changed as necessary.

Controller 20 calculates three-dimensional shape information of the object based on a focal position detected by focal position detector 7 and a detection result of optical sensor 4 at that position. Controller 20 acquires three-dimensional shape information by using the principle of "dot product", which is a kind of focusing method. In particular, in the field of dentistry, the object to be imaged by three-dimensional scanner 100 is an intraoral tissue, for example, it is a tooth. A tooth is a difficult-to-image body consisting of enamel and the like.

Specifically, the teeth have physical properties such as surface glossiness and translucency because teeth are made of enamel. Therefore, when a tooth is imaged with a three-dimensional scanner, it is impossible to acquire an image in which a pattern projected onto the tooth is clearly reflected due to the translucency of the enamel, and it has been difficult to correctly determine the focal position based on the principle of the focusing method. Further, a captured image is saturated in luminance due to the surface glossiness of the enamel, which makes it difficult to see the pattern projected on the tooth, and a circle of confusion occurring when a highly glossy point is slightly blurred interferes with the pattern, so that it has been likewise difficult to correctly determine the focal position in the focusing method. Therefore, in three-dimensional scanner 100, the measurement accuracy of the three-dimensional shape information is enhanced by changing the light emission amount of light source 1 based on the focal position detected by focal position detector 7.

Here, the focusing method includes various methods of various names such as "focus method", "confocal method", "SFF (Shape-From-Focus) method", and "DFF (Depth-From-Focus) method" as well as "dot product" disclosed in Japanese Patent No. 5654583 (Patent Literature 1), and a technique in which details of algorithms are improved, a technique in which a pattern of the surface of an object is used to determine the focal position instead of projecting a pattern, a technique in which dot-patterned light is generated by using pinholes or a lens array instead of the pattern, etc. are disclosed in various documents. All the techniques are common in that they relate to three-dimensional scanners for acquiring three-dimensional shape information by calculating the most focused position from a captured image, and they have the same problem that the measurement accuracy of the three-dimensional shape information deteriorates in some types of objects. Therefore, the configuration in the present disclosure can be applied.

In addition to the calculation of the three-dimensional shape information, controller 20 transmits a control signal to driver circuit 1a to control the light emission amount of light source 1, and transmits a control signal to motor driver 6c to control the position of focus lens 6a.

Controller 20 includes a CPU (Central Processing Unit) as a control center, a ROM (Read Only Memory) in which programs, control data, etc. for causing the CPU to operate are stored, a RAM (Random Access Memory) that functions as a work area for the CPU, an input/output interface for maintaining signal matching with peripheral devices, and the like. Further, controller 20 can output the acquired three-dimensional shape information to computer 30, and can receive information such as settings, commands and the like from computer 30. The programs to be executed by controller may be provided after being fixedly recorded in a tangible recording medium such as CD-ROM, DVD-ROM, or a semiconductor memory, or may be provided as a data signal superimposed on carrier waves through a communication network.

Note that at least a part of the calculation for processing a captured image to acquire three-dimensional shape information may be implemented as software by the CPU of controller 20, or may be implemented as hardware for performing processing separately from the CPU. At least some of the processing units such as the CPU and hardware may be incorporated inside handpiece 10. Furthermore, in FIG. 2, a cable for connecting handpiece 10 to computer 30 is illustrated in the handpiece 10, but handpiece 10 may be connected to computer 30 by wireless communication without providing any cable.

The three-dimensional shape information of the object acquired by controller 20 is displayed on a display unit of computer 30. The display unit may be a display incorporated in computer 30, a stationary display connected to computer 30, a head-mounted or glasses-type wearable display, or the like. Three-dimensional scanner 100 also has a power supply unit (not shown) for supplying power to drive light source 1, motor driver 6c, controller 20, and the like.

[Dimming Control of Light Source]

Figure 3:
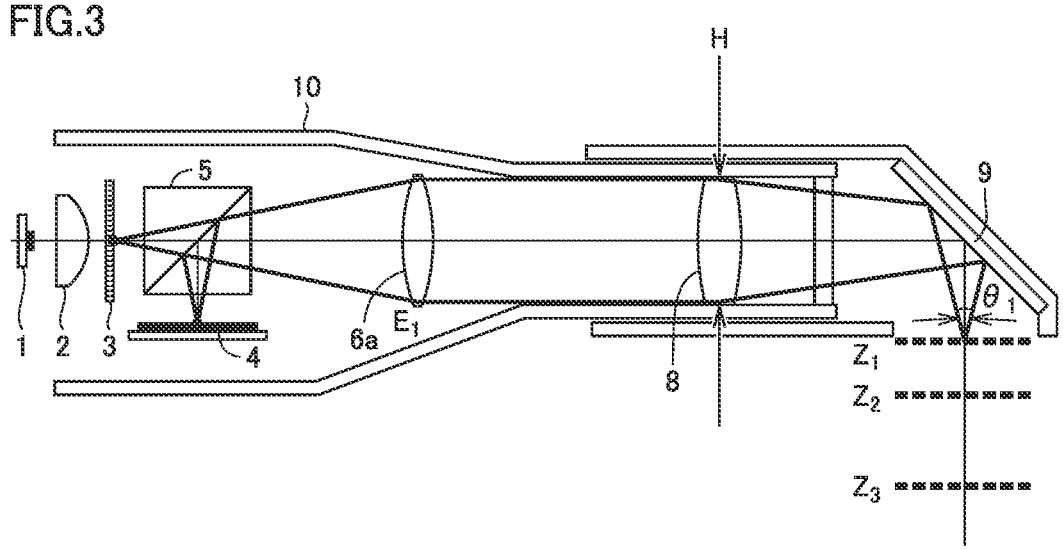
FIG. 3 is a schematic diagram for illustrating the brightness of a captured image when the focal position is close to an emission end face in the three-dimensional scanner.
Figure 4:
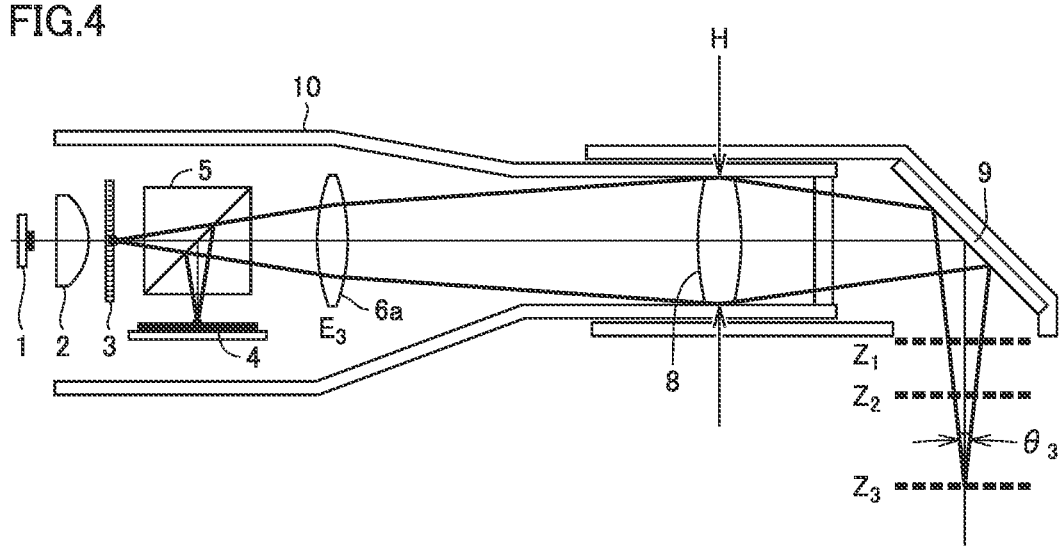
FIG. 4 is a schematic diagram for illustrating the brightness of a captured image when the focal position is far from the emission end face in the three-dimensional scanner.

Next, control (dimming control) for changing the light emission amount of light source 1 in three-dimensional scanner 100 will be described. First, the necessity for dimming control of light source 1 in three-dimensional scanner 100 will be described. FIG. 3 is a schematic diagram for illustrating the brightness of a captured image when the focal position is close to the emission end face in three-dimensional scanner 100. FIG. 4 is a schematic diagram for illustrating the brightness of a captured image when the focal position is far from the emission end face in three-dimensional scanner 100.

When the position of focus lens 6a is the position $E_1$ as shown in FIG. 3, one point on optical sensor 4 forms an image at the focal position $Z_1$ of the object. The brightness of an image captured by optical sensor 4 is determined by a flux of light within an angle $\theta$ ($=\theta_1$) at which an image is formed on optical sensor 4 among light reflected at various angles on the surface of the object. Therefore, the brightness of the image captured by optical sensor 4 increases as the angle $\theta$ of the flux of light increases.

On the other hand, when the position of focus lens 6a is the position $E_3$ as shown in FIG. 4, one point on optical sensor 4 forms an image at the focal position $Z_3$ of the object. Therefore, the angle $\theta$ of the flux of light becomes a smaller angle $\theta_3$ than the angle $\theta_1$ in the case of the focal position $Z_1$, so that the image captured by optical sensor 4 becomes dark.

In FIGS. 3 and 4, the angle θ of the flux of light is roughly determined by the ratio between the focal position ($Z_1$ to $Z_3$) and the aperture H of second lens 8 provided at the tip of handpiece 10. However, three-dimensional scanner 100 in the field of dentistry in which the tip of handpiece 10 must be inserted into a narrow oral cavity has a restriction that the aperture H of second lens 8 cannot be increased, and the difference in brightness of a captured image increases between image formation at the focal position $Z_1$ and image formation at the focal position $Z_3$. Further, from the viewpoint of preventing cross-infection, three-dimensional scanner 100 in the field of dentistry is advantageous in that a tip portion to be inserted into a living body is configured to be detachably attached to a handpiece for sterilization. However, since the wall thickness of a holder member outside the aperture H of second lens 8 shown in FIGS. 3 and 4 includes the thickness of two layers, it is further impossible to increase the aperture H in three-dimensional scanner 100 in the field of dentistry, and the difference in brightness of a captured image according to the focal position becomes remarkable. With reference to the figures, how the difference in brightness of a captured image according to the focal position affects a three-dimensional measurement result will be described hereinafter.

First, three-dimensional scanner 100 acquires three-dimensional shape information by a focusing method. In the focusing method, the in-focus degree is determined (focus determination is performed) based on the difference in brightness (contrast amount) between a black portion and a white portion of a pattern (for example, a checkered pattern) of an image captured by optical sensor 4. Therefore, three-dimensional scanner 100 affects the measurement accuracy of the acquired three-dimensional shape information depending on the brightness of the image captured by optical sensor 4.

Figure 5A:
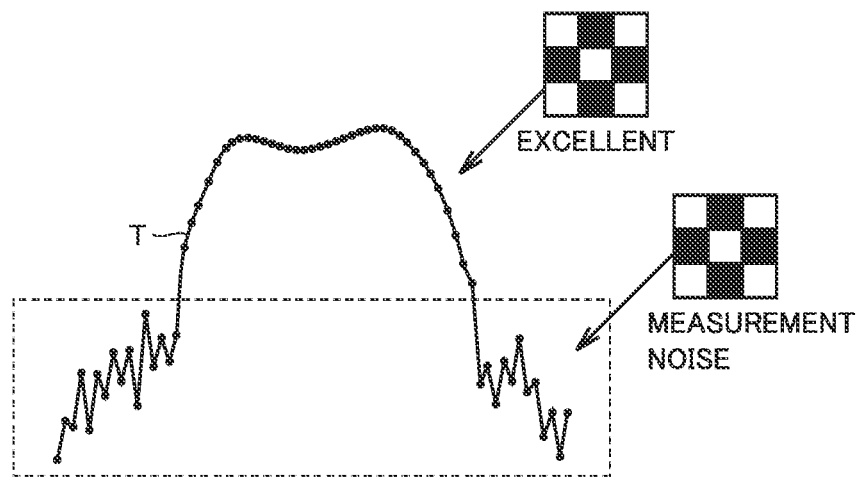
FIG. 5A is a schematic diagram for illustrating the relationship between the light emission amount of a light source and the state of a captured image in the three-dimensional scanner.
Figure 5B:
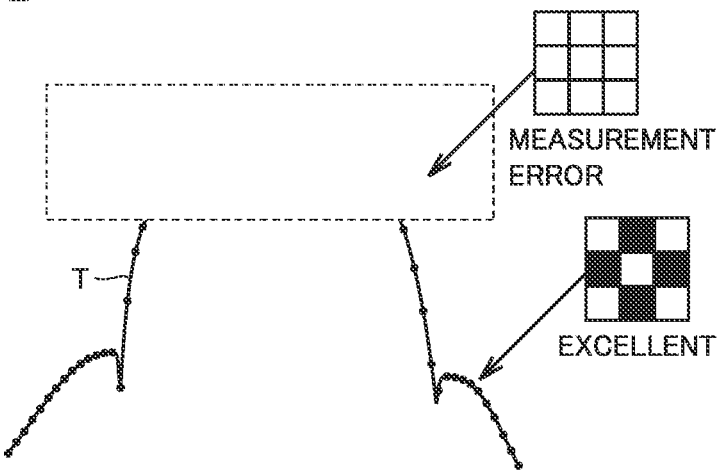
FIG. 5B is a schematic diagram for illustrating the relationship between the light emission amount of the light source and the state of the captured image in the three-dimensional scanner.
Figure 5C:
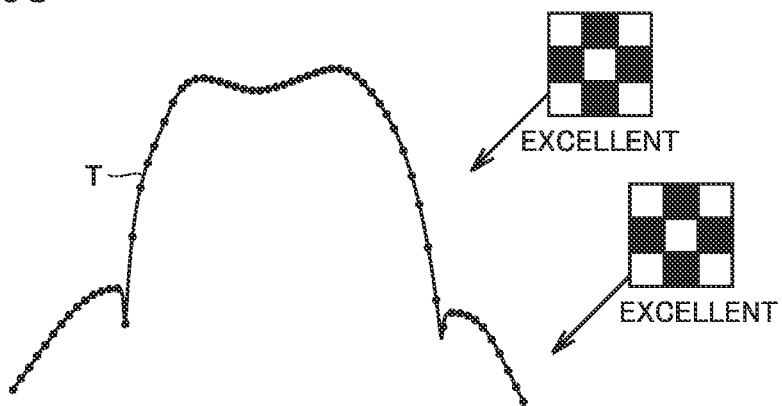
FIG. 5C is a schematic diagram for illustrating the relationship between the light emission amount of the light source and the state of the captured image in the three-dimensional scanner.

FIGS. 5A to 5C are schematic diagrams for illustrating the relationship between the light emission amount of a light source and the state of a captured image in a three-dimensional scanner. As shown in FIGS. 3 and 4, when the light emission amount of light source 1 is set to be constant, an image captured by optical sensor 4 is bright at the focal position $Z_1$ near the emission end face and is easily affected by luminance saturation which is caused by the glossiness of the enamel. Conversely, at the focal position $Z_3$ far from the emission end face, the image captured by optical sensor 4 is darker, and measurement noise increases, so that the contrast of the pattern deteriorates due to the translucency of the enamel. Therefore, in a case where a tooth T having enamel on the surface thereof is imaged by the three-dimensional scanner, if light source 1 is caused to emit dark light at all times for the purpose of avoiding luminance saturation of optical sensor 4 as shown in FIG. 5, an image close to the emission end face would be excellent, whereas an image far from the emission end face is darker, so that it is impossible to clearly detect the contrast of the pattern, and thus the measurement noise increases. It is assumed in FIG. 5A that the upper side in the figure is closer to the emission end face, and the lower side in the figure is farther from the emission end face.

Conversely, if light source 1 is caused to emit bright light at all times for the purpose of avoiding an increase in measurement noise as shown in FIG. 5B, an image far from the emission end face would be excellent, whereas an image close to the emission end face suffers luminance saturation in optical sensor 4, resulting in a measurement error. It is assumed in FIG. 5B that the upper side in the figure is closer to the emission end face, and the lower side in the figure is farther from the emission end face.

Figure 6:
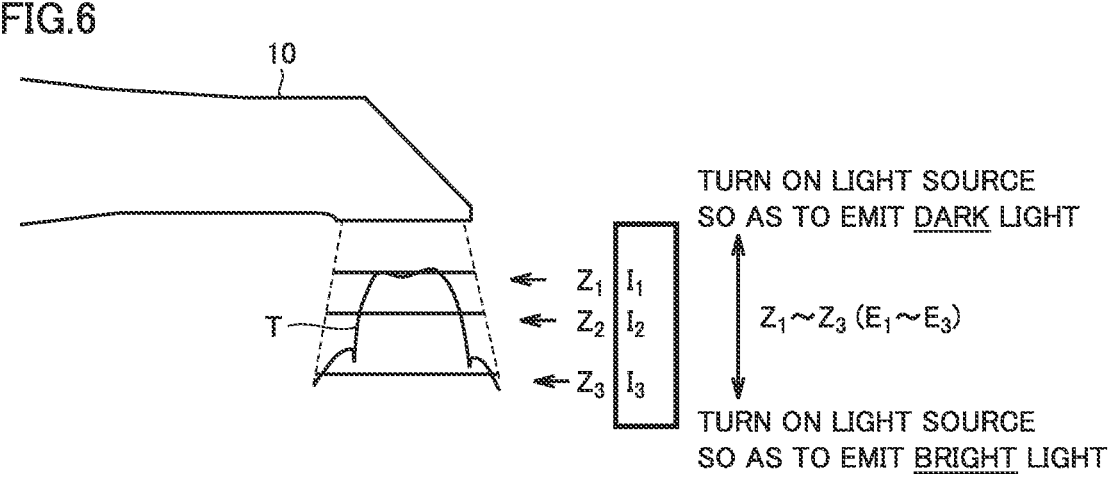
FIG. 6 is a schematic diagram for illustrating the relationship between the focal position and the light emission amount of the light source in the three-dimensional scanner according to the first embodiment.

Therefore, in three-dimensional scanner 100 according to the first embodiment, the amount of light from light source 1, which is reflected by the object and reaches optical sensor 4, is changed based on the focal position of variable focus lens 6. FIG. 6 is a schematic diagram for illustrating the relationship between the focal position and the light emission amount of light source 1 in three-dimensional scanner 100. In three-dimensional scanner 100, as shown in FIG. 6, in the case of the focal position $Z_1$ closer to the emission end face, the light emission amount of light source 1 is set to be smaller (light source 1 is turned on with a low current amount $I_1$) than those in the case of the focal positions $Z_2$ and $Z_3$, and in the case of the focal position $Z_3$ farther from the emission end face, the light emission amount of light source 1 is set to be larger than those in the case of the focal positions $Z_1$ and $Z_2$ (light source 1 is turned on with a high current amount $I_3$). In other words, controller 20 changes the light emission amount of light source 1 (via the current amounts $I_1$ to $I_3$ corresponding to the light emission amount) based on the focal positions $Z_1$ to $Z_3$ (corresponding to the positions $E_1$ to $E_3$ of focus lens 6a) detected by focal position detector 7.

Therefore, in the case of imaging the tooth T, as shown in FIG. 5C, when the focal position is close to the emission end face, the three-dimensional scanner makes the light emission amount of light source 1 smaller than that when the focal position is far from the emission end face, thereby acquiring an excellent image, and when the focal position is far from the emission end face, the three-dimensional scanner makes the light emission amount of light source 1 larger than that when the focal position is close to the emission end face, thereby acquiring an excellent image. It is assumed in FIG. 5C that the upper side in the figure is closer to the emission end face, and the lower side in the figure is farther from the emission end face.

Figure 7:
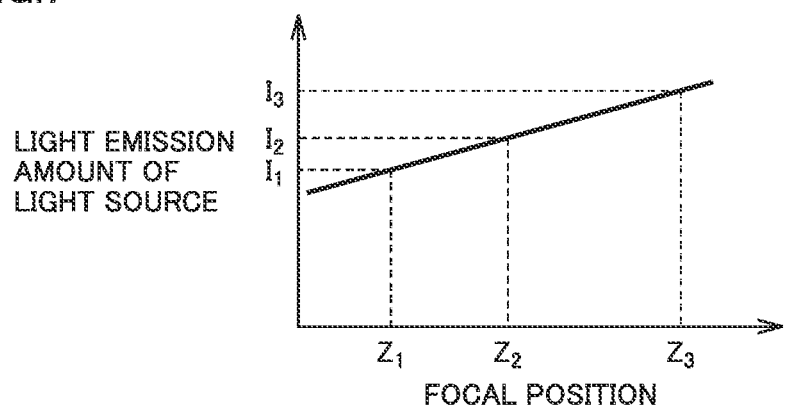
FIG. 7 is a graph showing an example of the relationship between the focal position and the light emission amount of the light source in the three-dimensional scanner according to the first embodiment.

FIG. 7 is a graph showing an example of the relationship between the focal position and the light emission amount of light source 1 in three-dimensional scanner 100 according to the first embodiment. As shown in FIG. 7, controller 20 presets a conversion table in which the light emission amount of light source 1 (the current amounts $I_1$ to $I_3$ corresponding to the light emission amount) linearly changes with respect to the focal positions $Z_1$ to $Z_3$ detected by focal position detector 7, or the like and performs dimming control on light source 1 according to the conversion table.

Next, the dimming control of light source 1 will be described with reference to a flowchart. FIG. 8 is a flowchart for illustrating the dimming control of the light source of three-dimensional scanner 100 according to the first embodiment. First, when a user starts scanning an object (for example, presses a start button or the like), controller 20 controls motor driver 6c to drive the slider to which focus lens 6a is fixed (step S11). Controller 20 turns on light source 1 (step S12).

Controller 20 acquires the current position of focus lens 6a with optical encoder (step S13). Controller 20 acquires an image of the object with optical sensor 4 (step S14). Controller 20 determines whether the number of acquired images has reached a predetermined number (step S15).

If the number of acquired images has not reached the predetermined number (NO in step S15), controller 20 specifies the focus position from the current position of focus lens 6a acquired in step S13, and changes the light emission amount of light source 1 (the current amount I corresponding to the light emission amount) based on the conversion table of the graph shown in FIG. 7 (step S16). Although it has been described that controller 20 specifies the focal position from the current position of focus lens 6a and changes the light emission amount of light source 1 based on the conversion table, the light emission amount of light source 1 (the current amount I corresponding to the light emission amount) may be changed based on the current position of focus lens 6a. The controller 20 then repeats steps S13 through S16 until the number of acquired images has reached the predetermined number.

When the number of acquired images has reached the predetermined number (YES in step S15), controller 20 performs focus determination from an acquired image group to acquire three-dimensional shape information (step S17).

Controller 20 may preset a conversion table in which the light emission amount of light source 1 (the current amounts $I_1$ to $I_3$ corresponding to the light emission amount) linearly changes with respect to the focal positions $Z_1$ to $Z_3$ detected by focal position detector 7 as shown in FIG. 7 or the like when a device is manufactured (that is, when it is shipped from a factory), and the conversion table may be changed at the time of maintenance. For example, light source 1 emits darker (dimmer) light due to age deterioration, and the conversion table is updated by a calibration process. Specifically, during the calibration process, a reference object such as a white plane plate is imaged by three-dimensional scanner 100, and the light emission amount of light source 1 is evaluated. For example, when the light emission amount of light source 1 which was 100% immediately after the device was manufactured has decreased to 80% due to aging, controller 20 updates the conversion table such that the light emission amounts of light source 1 (the current amounts $I_1$ to $I_3$ corresponding to the light emission amount) shown in FIG. 7 are multiplied by 1.25 (=100%/80%), respectively.

In addition to changing the conversion table during maintenance, controller 20 may store a plurality of types of conversion tables in the ROM in advance and change the conversion table according to an object to be scanned, or change the conversion table according to the type of light source, or change the conversion table based on the captured image. For example, controller 20 determines the reflectance of the object based on captured images of initial several frames during scanning, and when the reflectance is equal to or higher than a predetermined reflectance (in the case of excessive glare), controller 20 changes the conversion table to an appropriate conversion table among the plurality of types of conversion tables stored in ROM so as to emit darker (dimmer) light.

In addition to the above-described method, artificial intelligence (AI) may be installed in controller 20 of three-dimensional scanner 100 to determine an optimal conversion table from captured images based on machine-learned data. For example, when AI determines that the captured image represents the inside of a human's oral cavity, AI operates to refer to a conversion table for oral cavities, and when AI determines that the captured image represents a gypsum dental technical model which is brighter than the human's oral cavities, the AI operates to refer to a conversion table in which the light emission amount is suppressed as compared with the conversion table for oral cavities.

Figure 9A:
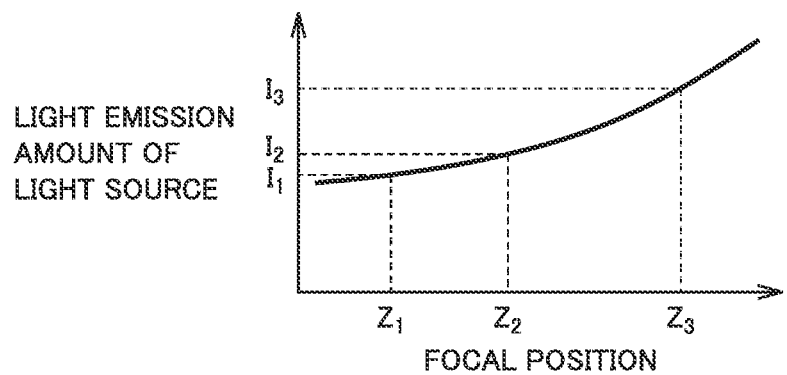
FIG. 9A is a graph showing a modification example of the relationship between the focal position and the light emission amount of the light source in the three-dimensional scanner according to the first embodiment.
Figure 9B:
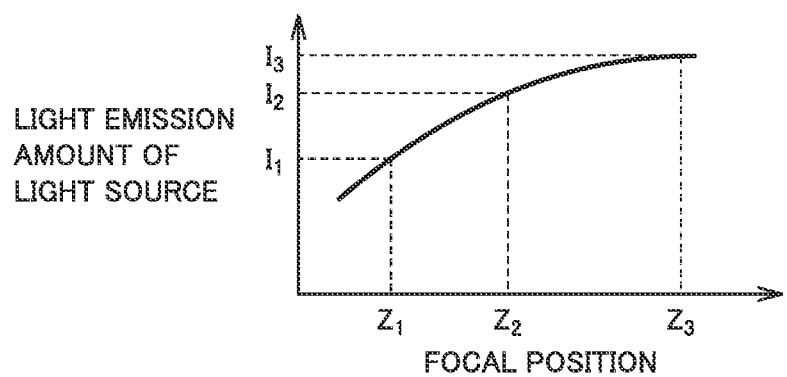
FIG. 9B is a graph showing a modification example of the relationship between the focal position and the light emission amount of the light source in the three-dimensional scanner according to the first embodiment.
Figure 9C:
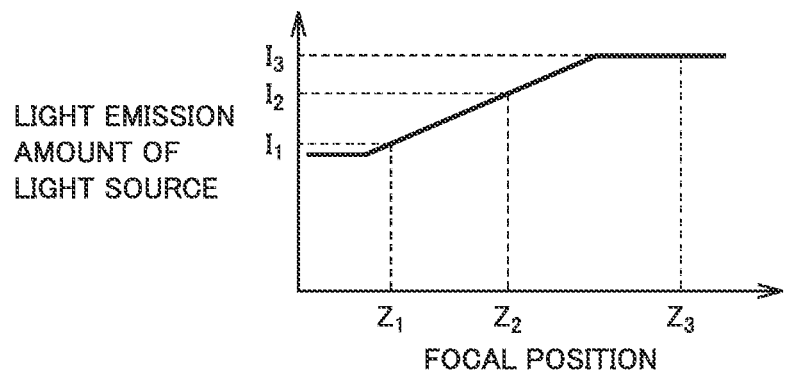
FIG. 9C is a graph showing a modification example of the relationship between the focal position and the light emission amount of the light source in the three-dimensional scanner according to the first embodiment.

Further, in FIG. 7, a linear relationship between the focal position and the light emission amount is shown as an example of the conversion table, but a conversion table in which they are nonlinearly related to each other may also be used. FIGS. 9A to 9C are graphs showing modification examples of the relationship between the focal position and the light emission amount of the light source in three-dimensional scanner 100 according to the first embodiment. In FIG. 9A, the change in the light emission amount of light source 1 (the current amounts $I_1$ to $I_3$ corresponding to the emission amount) increases as the focal position detected by focal position detector 7 shifts from the focal position $Z_1$ to the focal position $Z_3$. In FIG. 9B, the change in the light emission amount of light source 1 (the current amounts $I_1$ to $I_3$ corresponding to the emission amount) decreases as the focal position detected by focal position detector 7 shifts from the focal position $Z_1$ to the focal position $Z_3$. In FIG. 9C, the light emission amount of light source 1 does not change but is equal to a constant value around the focal position $Z_3$ detected by focal position detector 7. By setting such a nonlinear conversion table, it is possible to accurately acquire three-dimensional shape information even for three-dimensional scanner 100 having a complicated optical system in which the brightness changes nonlinearly due to vignetting or the like.

Second Embodiment

Figure 10:
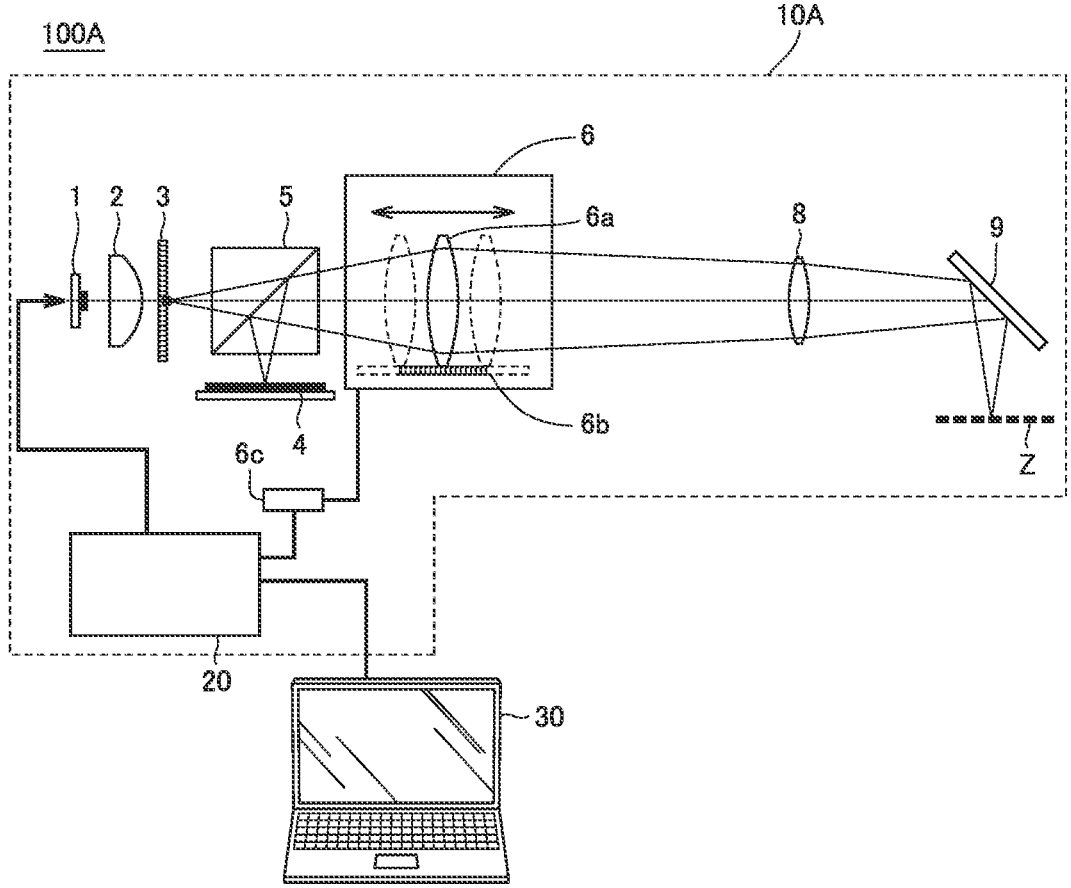
FIG. 10 is a schematic diagram showing a configuration of a three-dimensional scanner according to a second embodiment.

Three-dimensional scanner 100 according to the first embodiment has been described to be configured so that the focal position of variable focus lens 6 is detected by using focal position detector 7 and the light emission amount of light source 1 is changed based on the detected focal position. However, a three-dimensional scanner according to a second embodiment is configured so that the light emission amount of light source 1 is changed based on a control signal of variable focus lens 6 without detecting the focal position of variable focus lens 6 by using focal position detector 7. FIG. 10 is a schematic diagram showing a configuration of a three-dimensional scanner 100A according to the second embodiment. In the configuration of three-dimensional scanner 100A shown in FIG. 10, the same components as those of three-dimensional scanner 100 shown in FIG. 1 are represented by the same reference signs, and detailed description thereof is not repeated.

Three-dimensional scanner 100A has the same configuration as three-dimensional scanner 100 shown in FIG. 1 except that it is not provided with focal position detector 7 out of the optical components in handpiece 10A. Instead of detecting the focal position of variable focus lens 6 by focal position detector 7, three-dimensional scanner 100A changes the amount of light from light source 1 which is reflected by the object and reaches optical sensor 4 based on a control signal for changing the focal position of variable focus lens 6.

Specifically, controller 20 transmits a control signal to motor driver 6c to control the position of focus lens 6a. Therefore, the positions $E_1$ to $E_3$ of focus lens 6a can be indirectly specified based on the control signal to be transmitted to motor driver 6c, and controller 20 can change the light emission amount of light source 1 based on the control signal to be transmitted to motor driver 6c.

Modification Example

Figure 11:
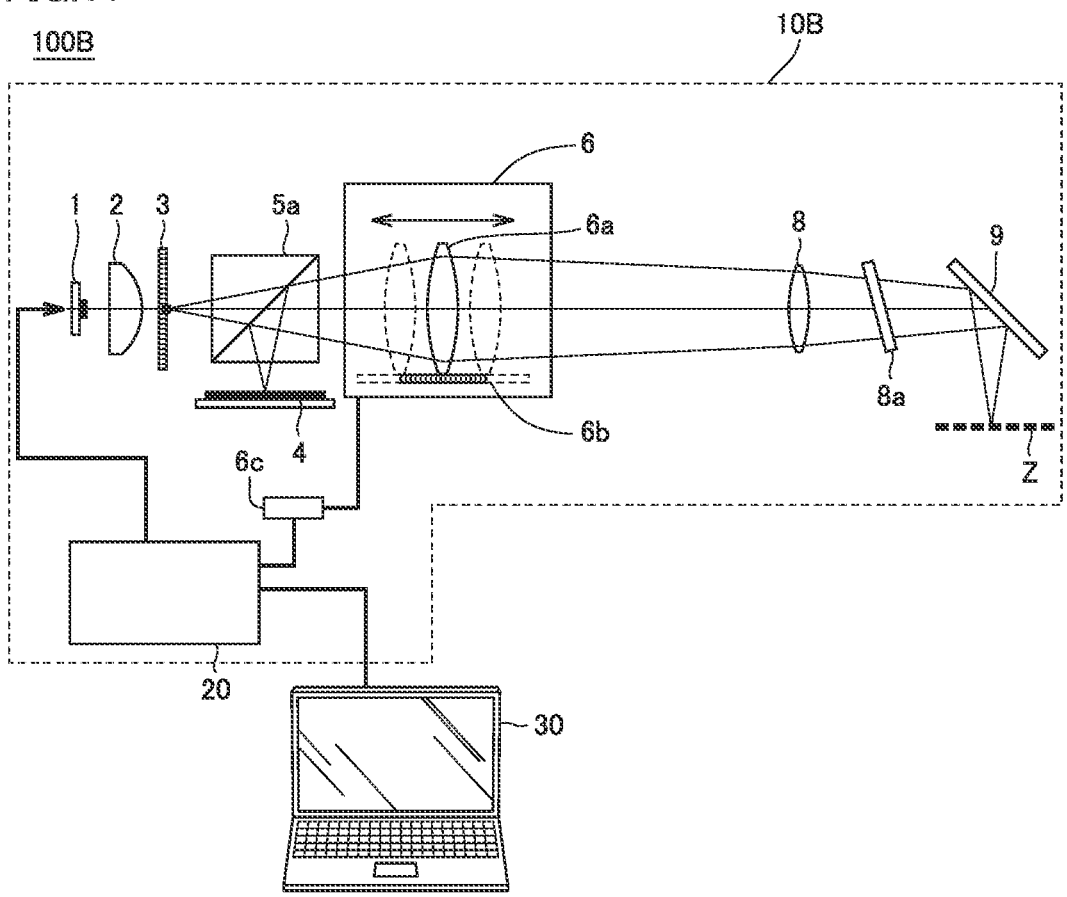
FIG. 11 is a schematic diagram showing a configuration of a three-dimensional scanner according to a modification example of the second embodiment.

In the field of dentistry, an object to be imaged by a three-dimensional scanner is a tooth, which is a difficult-to-image body consisting of enamel or the like. Therefore, it is effective that polarized light is used to more clearly image a pattern projected on an enamel material which is a translucent difficult-to-image substance. Therefore, a modification example of the three-dimensional scanner using polarized light will be described. FIG. 11 is a schematic diagram showing a configuration of a three-dimensional scanner 100B according to a modification example of the second embodiment. In the configuration of three-dimensional scanner 100B shown in FIG. 11, the same components as those of three-dimensional scanner 100A shown in FIG. 10 are represented by the same reference signs, and detailed description thereof is not repeated.

Three-dimensional scanner 100B has the same configuration as three-dimensional scanner 100A shown in FIG. 10 except that it is further provided with a polarization beam splitter 5a and a wave plate 8a as optical components in handpiece 10B. Polarization beam splitter 5a is provided between light source 1, optical sensor 4 and variable focus lens 6 so that an optical path extending from light source 1 to the object and an optical path extending from the object to optical sensor 4 are separated from each other. Further, polarization beam splitter 5a may be configured to increase the polarization extinction ratio by adding a pre-polarizer/post-polarizer. Wave plate 8a is provided between variable focus lens 6 and the object such that light reaching the object and light reflected from the object passes through wave plate 8a. Further, it is possible that wave plate 8a is tilted with respect to the optical axis so that Fresnel reflected light from wave plate 8a is prevented from being reflected onto optical sensor 4. Note that wave plate 8a may be tilted in a direction different from that shown in FIG. 11. Further, it is possible that wave plate 8a is a quarter wave plate. By configuring three-dimensional scanner 100B as described above, it is possible to selectively guide necessary light to optical sensor 4 by utilizing a phenomenon wherein a polarization state of necessary light reflected from the surface of a tooth and a polarization state of unnecessary light scattered and reflected inside the tooth are different from each other. Therefore, three-dimensional scanner 100B can enhance the measurement accuracy of the three-dimensional shape information. However, such a configuration may cause a phenomenon wherein specular reflection (extremely glaring reflection) is emphasized due to the glossiness of enamel and luminance saturation tends to occur.

In three-dimensional scanner 100B, the amount of light from light source 1 which is reflected by the object and reaches optical sensor 4 is changed based on the control signal for changing the focal position of variable focus lens 6, which can avoid the problem wherein specular reflection (extremely glaring reflection) caused by the glossiness of enamel is emphasized and luminance saturation occurs in optical sensor 4. Therefore, the configuration of the three-dimensional scanner that changes the amount of light from light source 1 according to the focal position is a particularly useful solution for an optical system using polarized light. Therefore, not only three-dimensional scanner 100A shown in FIG. 10 but also other three-dimensional scanners described in the present disclosure such as three-dimensional scanner 100 shown in FIG. 1 may be likewise further provided with polarization beam splitter 5a and wave plate 8a.

Third Embodiment

Figure 12:
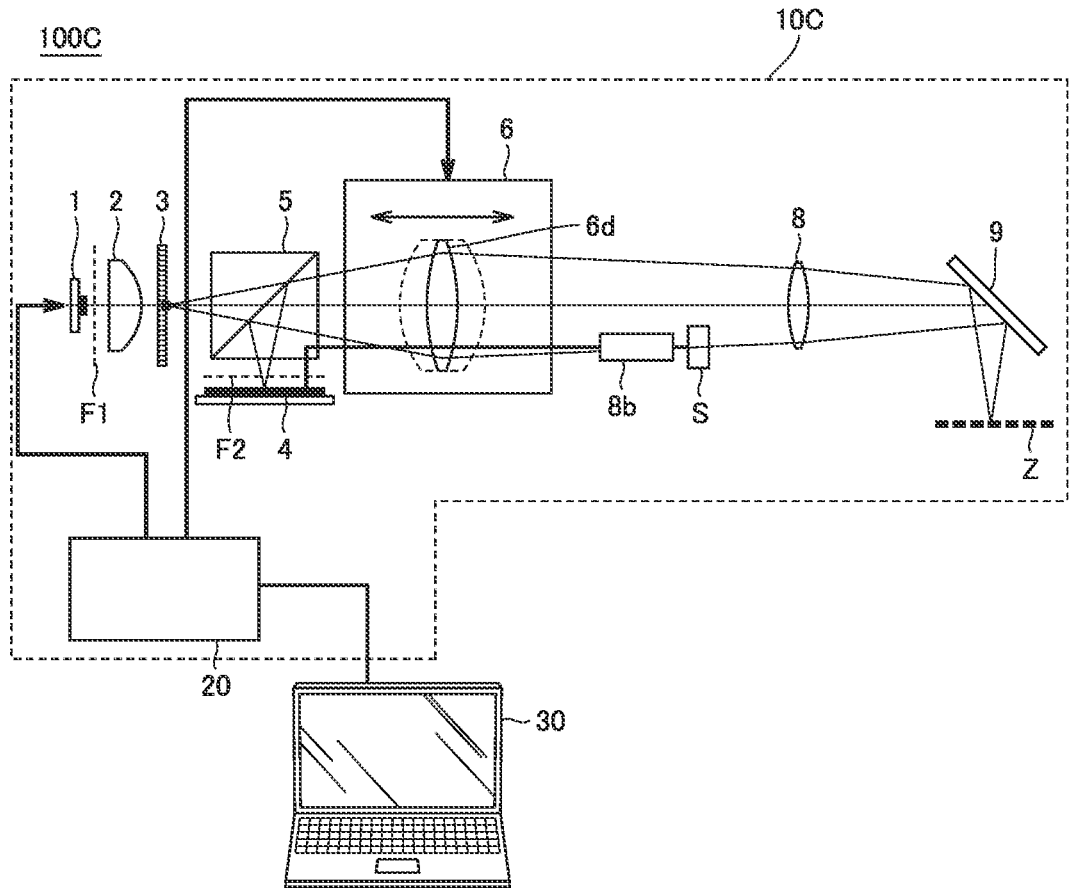
FIG. 12 is a schematic diagram showing a configuration of a three-dimensional scanner according to a third embodiment.

With respect to three-dimensional scanner 100 according to the first embodiment, the configuration in which the focal position of the object is changed by mechanically moving the position of the lens has been described. However, a three-dimensional scanner according to a third embodiment has a configuration using a variable focus lens in which the position of the lens is not mechanically moved. FIG. 12 is a schematic diagram showing a configuration of a three-dimensional scanner 100C according to a third embodiment. In the configuration of three-dimensional scanner 100C shown in FIG. 12, the same components as those of three-dimensional scanner 100 shown in FIG. 1 are represented by the same reference signs, and detailed description thereof is not repeated.

In three-dimensional scanner 100C, a liquid lens 6d is used as variable focus lens 6 which does not mechanically move the position of the lens instead of variable focus lens 6a, which is fixed to the slider and moved along rail 6b extending in the optical axis direction. An example of liquid lens 6d includes, for example, a method for providing an electrode on the side surface of a container in which an aqueous solution and oil are enclosed, and applying a voltage to the electrode to change the shape of the interface between the aqueous solution and the oil, thereby changing the focal position (in FIG. 12, liquid lens 6d is schematically shown as a single biconvex lens, and detailed structures of the aqueous solution, the oil, and the like are omitted).

In three-dimensional scanner 100C, liquid lens 6d is adopted as variable focus lens 6, so that a reference portion S to be irradiated with a part of light from light source 1 is provided as a focal position detector. A known pattern is formed on reference portion S. The focal position detector can accurately grasp the state (focal position) of liquid lens 6d by utilizing an imaging result of the pattern provided on reference portion S.

Specifically, light output from a part of light source 1 passes through liquid lens 6d, and is applied to reference portion S and reflected by reference portion S. The light reflected by reference portion S passes through liquid lens 6d again and is detected by a part of optical sensor 4. Note that reference portion S is provided in the housing of handpiece 10C, so that an optical path extending from a part of light source 1 through reference portion S to a part of optical sensor 4 is shorter than an optical path extending from light source 1 through the object to optical sensor 4. Therefore, an optical path length adjusting unit 8b for adjusting the optical path length extending from light source 1 through the object to optical sensor 4 and the optical path length extending from a part of light source 1 through reference portion S to a part of optical sensor 4 is provided on an optical path extending from a part of light source 1 through reference portion S to a part of optical sensor 4.

Optical path length adjusting unit 8b may be any optical component as long as it can adjust the optical path length of the optical path extending from a part of light source 1 through reference portion S to a part of optical sensor 4, and examples of optical path length adjusting unit 8b include a glass block, a light guide, a lens, a lens array, an offset mirror/prism, a dichroic mirror, a delay line, a pentaprism and the like. Both of the optical path lengths are almost matched with each other by using optical path length adjusting unit 8b, whereby substantially in-focus images can be captured by optical sensor 4 for both the object and reference portion S. In other words, a corresponding relationship can be established between the in-focus position on the object and the in-focus position on reference portion S. Therefore, an image of reference portion S captured by using a part of optical sensor 4 is analyzed, and an in-focus position on reference portion S is determined, whereby it is possible to accurately grasp the state (focal position) of liquid lens 6d.

In three-dimensional scanner 100C, the focal position of liquid lens 6d is specified from the image of reference portion S captured by a part of optical sensor 4, and the amount of light from light source 1 which is reflected by the object and reaches optical sensor 4 is changed based on the specified focal position of liquid lens 6d. If the focal position can be roughly specified based on the control signal for liquid lens 6d, three-dimensional scanner 100C may change the amount of light from light source 1 reflected by the object and reaching optical sensor 4 based on the control signal of liquid lens 6d.

Modification Example

It has been described that in three-dimensional scanners according to the first to third embodiments, the light emission amount of light source 1 is changed as means for changing the amount of light from light source 1 which is reflected by the object and reaches optical sensor 4. In other words, controller 20 controls driver circuit 1a for driving light source 1 to change the amount of current I to be supplied to light source 1, thereby changing the light emission amount of light source 1. However, the means for changing the amount of light from light source 1 which is reflected by the object and reaches optical sensor 4 is not limited to this manner, and for example, a dimming filter (dimming filters F1, F2 shown in FIG. 12) may be further provided on at least one of the optical path extending from light source 1 to the object and the optical path extending from the object to optical sensor 4. Controller 20 may change the amount of light transmitted through the dimming filters F1, F2 to change the amount of light from light source 1 which is reflected by the object and reaches optical sensor 4. For example, a liquid crystal type dimming filter or an electronic shutter can be used for the dimming filters F1 and F2. Furthermore, controller 20 may change a detection period of optical sensor 4 (so-called exposure time/time of an electronic shutter equipped in optical sensor 4) to change the amount of light from light source 1 which is reflected by the object and reaches optical sensor 4.

Further, objects to be imaged by the three-dimensional scanners according to the first to third embodiments are not limited to teeth and gums in oral cavities, but may be biomedical tissues such as ear canals, objects whose surfaces are wetted with liquid, and industrial products subjected to glossy coating, coating or surface polishing, and the like, and the present disclosure is widely applicable to applications for performing three-dimensional measurement of difficult-to-image objects having glossiness/translucency, etc.

Although the present disclosure has been described and illustrated in detail, it is clearly understood that the same is by way of illustration and example only and is not to be taken by way of limitation, the scope of the present disclosure being interpreted by the terms of the appended claims.

What is claimed is:

1. A three-dimensional scanner for acquiring three-dimensional shape information of an object using focusing, comprising:
   a light source configured to emit light from an emission end face of a housing to the object;
   a sensor configured to detect light from the light source reflected by the object;
   a reciprocating variable focus lens that is provided between the object and the sensor and that changes a focal position based on the object; and
   a controller configured to change the focal position of the variable focus lens in a process of acquiring the three-dimensional shape information of the object,
   wherein the controller is configured to continuously change an amount of light from the light source that is reflected by the object and reaches the sensor based on a change in the focal position of the reciprocating variable focus lens.

2. The three-dimensional scanner according to claim 1, further comprising a focal position detector configured to detect the focal position of the reciprocating variable focus lens,
   wherein the controller changes the amount of light from the light source that is reflected by the object and reaches the sensor based on the focal position detected by the focal position detector.

3. The three-dimensional scanner according to claim 2, wherein the focal position detector includes a lens position sensor configured to detect a position of the reciprocating variable focus lens, and
   the controller specifies the focal position of the reciprocating variable focus lens based on an output from the lens position sensor.

4. The three-dimensional scanner according to claim 2, wherein the focal position detector includes a reference portion to be irradiated with a part of light from the light source, and
   the controller specifies the focal position of the reciprocating variable focus lens based on an output from a part of the sensor that has detected light reflected by the reference portion.

5. The three-dimensional scanner according to claim 2, further comprising a dimming filter in at least one of an optical path extending from the light source to the object and an optical path extending from the object to the sensor,
   wherein the controller changes an amount of light transmitted through the dimming filter to change the amount of light from the light source that is reflected by the object and reaches the sensor.

6. The three-dimensional scanner according to claim 2, wherein the controller changes a detection period of the sensor to change the amount of light from the light source that is reflected by the object and reaches the sensor.

7. The three-dimensional scanner according to claim 2, wherein the controller changes the amount of light from the light source that is reflected by the object and reaches the sensor based on a predetermined conversion table.

8. The three-dimensional scanner according to claim 1, wherein the controller changes a detection period of the sensor to change the amount of light from the light source that is reflected by the object and reaches the sensor.

9. The three-dimensional scanner according to claim 1, wherein the controller changes the amount of light from the light source that is reflected by the object and reaches the sensor based on a conversion table.

10. The three-dimensional scanner according to claim 9, wherein the conversion table is set so as to reduce the amount of light from the light source when the focal position of the reciprocating variable focus lens is closer to the emission end face, and increase the amount of light from the light source when the focal position of the reciprocating variable focus lens is further from the emission end face.

11. The three-dimensional scanner according to claim 9, wherein the controller is configured to change the conversion table by a calibration.

12. The three-dimensional scanner according to claim 9, wherein the controller is configured to change the conversion table based on a captured image.

13. The three-dimensional scanner according to claim 12, wherein the controller is configured to change the conversion table based on image recognition by machine learning on the captured image.

14. The three-dimensional scanner according to claim 1, further comprising:
- a polarization beam splitter that is provided between the light source or the sensor and the reciprocating variable focus lens and separates an optical path extending from the light source to the object and an optical path extending from the object to the sensor from each other; and
- a wave plate that is provided between the reciprocating variable focus lens and the object such that light reaching the object and light reflected from the object passes through the wave plate.

15. The three-dimensional scanner according to claim 1, wherein the object is an intraoral tissue.

16. The three-dimensional scanner according to claim 1, wherein the controller changes the amount of light from the light source that is reflected by the object and reaches the sensor based on a control signal for changing the focal position of the reciprocating variable focus lens.

17. The three-dimensional scanner according to claim 1, wherein the controller changes a light emission amount of the light source to change the amount of light from the light source that is reflected by the object and reaches the sensor.

18. The three-dimensional scanner according to claim 1, further comprising a dimming filter in at least one of an optical path extending from the light source to the object and an optical path extending from the object to the sensor,
- wherein the controller changes an amount of light transmitted through the dimming filter to change the amount of light from the light source that is reflected by the object and reaches the sensor.

19. A control method for a three-dimensional scanner comprising a light source configured to emit light from an emission end face of a housing to an object, a sensor configured to detect light from the light source reflected by the object, a reciprocating variable focus lens that is provided between the object and the sensor and that changes a focal position based on the object, and a controller configured to change the focal position of the reciprocating variable focus lens in a process of acquiring three-dimensional shape information of the object, the three-dimensional scanner acquiring three-dimensional shape information of the object by using a focusing process, the control method comprising:
- acquiring information on the focal position of the reciprocating variable focus lens; and
- continuously changing an amount of light from the light source that is reflected by the object and reaches the sensor based on the acquired information.

20. A non-transitory recording medium for recording programs executable by a computer included in a three-dimensional scanner comprising a light source that emits light from an emission end face of a housing to an object, a sensor that detects light from the light source reflected by the object, and a reciprocating variable focus lens that is provided between the object and the sensor and changes a focal position based on the object, the three-dimensional scanner acquiring three-dimensional shape information by using a focusing process, the programs causing the computer to:
- change the focal position of the reciprocating variable focus lens in a process of acquiring the three-dimensional shape information of the object; and
- continuously change an amount of light from the light source that is reflected by the object and reaches the sensor based on a change in the focal position of the variable focus lens.

* * * * *